(12) United States Patent
Kuhn et al.

(10) Patent No.: US 9,351,801 B2
(45) Date of Patent: May 31, 2016

(54) DENTAL HAND INSTRUMENT HAVING AN ELONGATE HANDLE SLEEVE

(75) Inventors: Bernhard Kuhn, Biberach (DE); Thomas Classen, Hebertingen (DE)

(73) Assignee: KALTENBACH & VOIGT GMBH, Biberach (DE)

( * ) Notice: Subject to any disclaimer, the term of this patent is extended or adjusted under 35 U.S.C. 154(b) by 0 days.

(21) Appl. No.: 13/428,639

(22) Filed: Mar. 23, 2012

(65) Prior Publication Data

US 2012/0288822 A1    Nov. 15, 2012

(30) Foreign Application Priority Data

May 11, 2011  (DE) .......................... 10 2011 075 670

(51) Int. Cl.
  *A61C 1/00*    (2006.01)
  *A61C 1/18*    (2006.01)
(52) U.S. Cl.
  CPC ...................................... *A61C 1/185* (2013.01)
(58) Field of Classification Search
  CPC ...................................................... A61C 1/185
  USPC ........... 433/29, 103–105, 108, 114–116, 118, 433/122, 124, 126, 131, 133, 134
  See application file for complete search history.

(56) References Cited

U.S. PATENT DOCUMENTS

| 4,211,009 | A | * | 7/1980 | Leonard | 433/126 |
| 4,693,871 | A | * | 9/1987 | Geller | 433/116 |
| 5,616,029 | A | * | 4/1997 | Suzuki | 433/122 |
| 6,050,989 | A | * | 4/2000 | Fox et al. | 606/1 |
| 6,948,934 | B2 | * | 9/2005 | Wade | 433/116 |
| 2005/0026110 | A1 | * | 2/2005 | Schatz et al. | 433/115 |

FOREIGN PATENT DOCUMENTS

JP    2010046269 A    3/2010

OTHER PUBLICATIONS

Dictionary.cambridge.org. Adjoin, Dec. 30, 2012 [retrieved on Dec. 30, 2012]. Retrieved from the Internet: http://dictionary.cambridge.org/dictionary/british/adjoin.*
Notice of Reasons for Rejection for Japanese Patent Application No. 2012-108717, dated Jun. 25, 2013.

* cited by examiner

*Primary Examiner* — Heidi M Eide
(74) *Attorney, Agent, or Firm* — Marshall, Gerstein & Borun LLP

(57) ABSTRACT

A dental hand instrument having an elongate handle sleeve, at the front end of which there is disposed a tool holder for holding a treatment tool, for example a dental drill, there is disposed inside the handle sleeve a driving mechanism for driving the treatment tool, the driving mechanism having at least two rotatably mounted shafts that are coupled to each other, and a sealing element is disposed in the coupling region of the two shafts inside the handle sleeve.

8 Claims, 3 Drawing Sheets

DENTAL HAND INSTRUMENT HAVING AN ELONGATE HANDLE SLEEVE

BACKGROUND OF THE INVENTION

1. Field of the Invention

The invention relates to a dental hand instrument, which has an elongate handle sleeve, at the front end of which there are disposed means for holding a treatment tool, for example a dental drill. Disposed inside the handle sleeve are means for driving the treatment tool, which means have at least two rotatably mounted shafts that are coupled to each other.

2. Related Technology

Such a dental hand instrument is already known, and is represented schematically in FIG. 7. Represented in this case is a so-called angled piece 100, in which the handle sleeve 101 is slightly offset in the central region. Disposed at the front end of the handle sleeve 101 is the head region 102, which is realized for rotatably receiving a treatment tool, for example a dental drill. The driving of the drill—not shown—is effected by means of a drive train, which, in the exemplary embodiment shown, has two shafts 105 and 106 that are coupled to each other. The rear shaft 105 in this case is coupled, at its back end, to a drive, for example an electric motor and, at the front end, is coupled to the front shaft 106 via a transmission 107. The rotation of the shafts is then transferred to the drill via a further transmission 108 at the head region 102. Furthermore, cavities and lines, for carrying media and/or light, extend through the handpiece. The drawing figure shows, for example, an optical waveguide 109, via which light is directed onto the treatment site to be treated by the drill.

In the case of such a handpiece 100, a distinction is made between the so-called functional region, i.e. the region in which the power train comprising the necessary elements is located, and the further cavities. The further cavities constitute spaces in which are located the lines for media, such as spray air and water, and the light line and joint gaps. It is necessary for a seal to be effected between the functional region and these further cavities.

The above-mentioned seal is necessary since, during a maintenance process for the handpiece 100, the functional region is flushed by means of positive pressure from the motor connection side. Ideally, the oil and cleaning fluid used for this purpose should emerge solely at the top of the head region 102. Leakages or connections between the functional region and the cavities have a very disadvantageous and adverse effect upon the manipulation of the instrument, since oil could emerge at joint gaps and, owing to the surface of the handle region having become oiled as a result, this makes it more difficult to manipulate the handpiece and, in addition, also requires increased re-oiling.

In particular, in the case of the angled handpiece represented in FIG. 7, this sealing is extremely difficult because of the large differences in the toothing diameters in the knee region, in which the two shafts 105 and 106 are coupled. Hitherto, this problem has been solved in that O-rings have been inserted facing outwardly at interfaces for the purpose of sealing. In addition, complex elastic shaped pieces have been used, or partial encapsulation of the connection point has been effected for the purpose of sealing. Such measures have been unsatisfactory, however, and in some cases have had the result of greatly impeding the assembly and disassembly of the handpiece or, in some cases, have even made this impossible.

SUMMARY OF THE INVENTION

The invention is therefore based on the object, in the case of such a handpiece, of providing a new type of solution for sealing the functional region in respect of the cavities.

The solution according to the invention is based on the concept of disposing an additional sealing element directly at the coupling region of the two shafts of the drive train, inside the handle sleeve. This sealing element in this case is designed in such a way that cleaning and care agent is prevented from emerging directly in the coupling region, so that further measures for sealing are no longer necessary. A further advantage of this solution in this case lies in that there is the possibility of reducing the volume of the functional space through which there is a flow, this ultimately reducing the oil requirement for the instrument. Assembly and disassembly of the hand instrument is not impeded by this additional sealing element.

There is accordingly provided, according to the invention, a dental hand instrument having an elongate handle sleeve, at the front end of which there are disposed means for holding a treatment tool, for example a dental drill, there being disposed inside the handle sleeve means for driving the treatment tool, which means have at least two rotatably mounted shafts that are coupled to each other, and, according to the invention, a sealing element being disposed in the coupling region of the two shafts, inside the handle sleeve.

Preferably, the sealing element has an approximately cylindrical lateral surface, which is realized to be received in a corresponding cylindrical bore of the handpiece. The sealing element in this case can further have a first cylindrical extension, which adjoins the lateral surface and which is aligned substantially parallel to a first of the two shafts. Preferably, the sealing element also has a second cylindrical extension, which is aligned substantially parallel to the second of the two shafts. The two shafts in this case can be aligned at an angle in relation to each other, i.e. the sealing element is provided for use in an angled piece. The invention is not limited exclusively to such angled pieces, however, but can be used whenever two drive elements are coupled inside a dental hand instrument and special measures for sealing are helpful in this region.

The sealing element can be composed of a slightly elastic material and, further, configured so as to ensure positioned or defined insertion in the dental instrument. These measures can be embodied in, for example, corresponding reliefs, elevations, bores, hollows, pins, balls or the like.

BRIEF DESCRIPTION OF THE DRAWINGS

The invention is explained more fully below with reference to the appended drawings, wherein.

DETAILED DESCRIPTION

Figure 1:
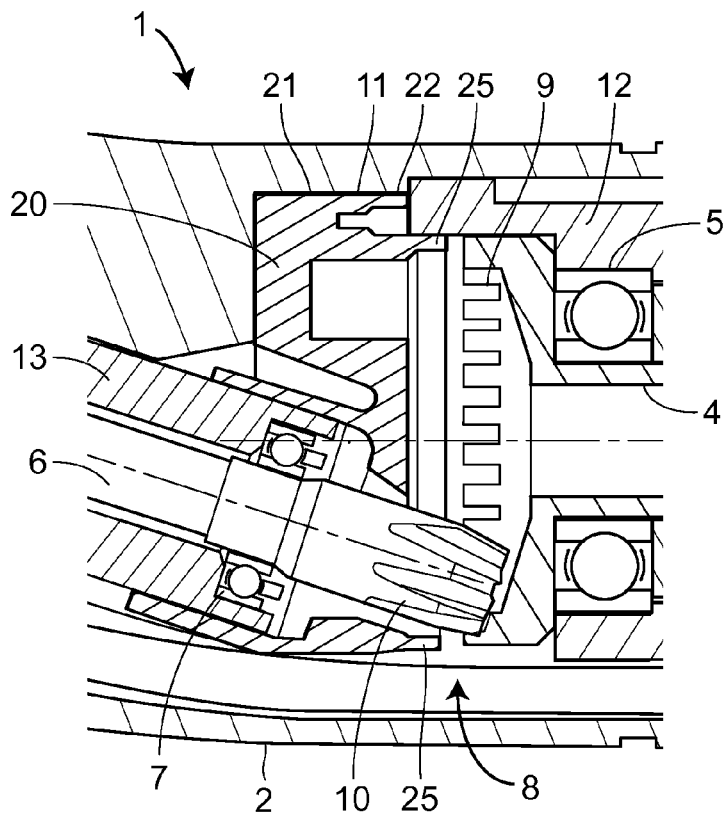
FIG. 1 shows the knee region of a dental angled piece, in which a sealing element according to the invention is used.
Figure 2:
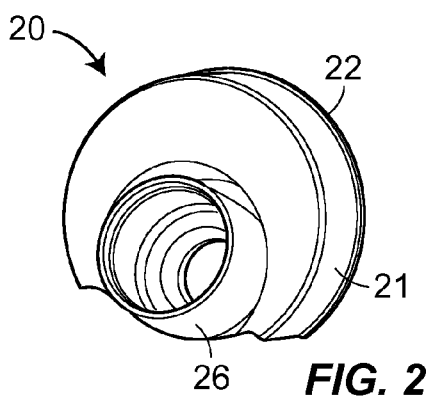
FIG. 2 shows a first perspective view of a sealing element according to the invention.
Figure 3:
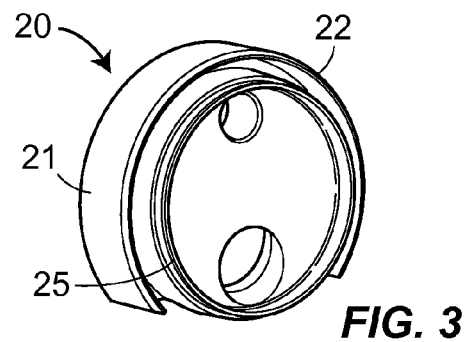
FIG. 3 shows a second perspective view of the sealing element of FIG. 2.
Figure 4:
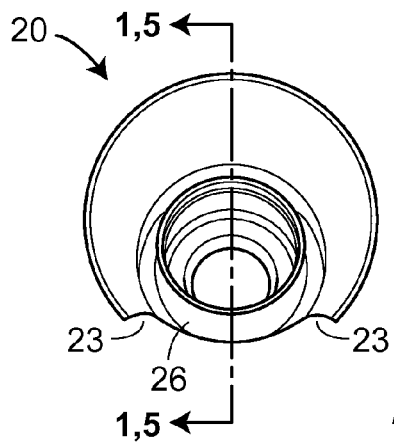
FIG. 4 shows a third perspective view of the sealing element of FIG. 2.
Figure 5:
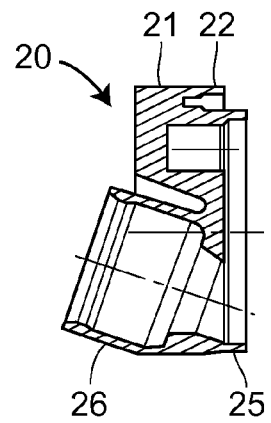
FIG. 5 shows a section representation of the sealing element.
Figure 7:
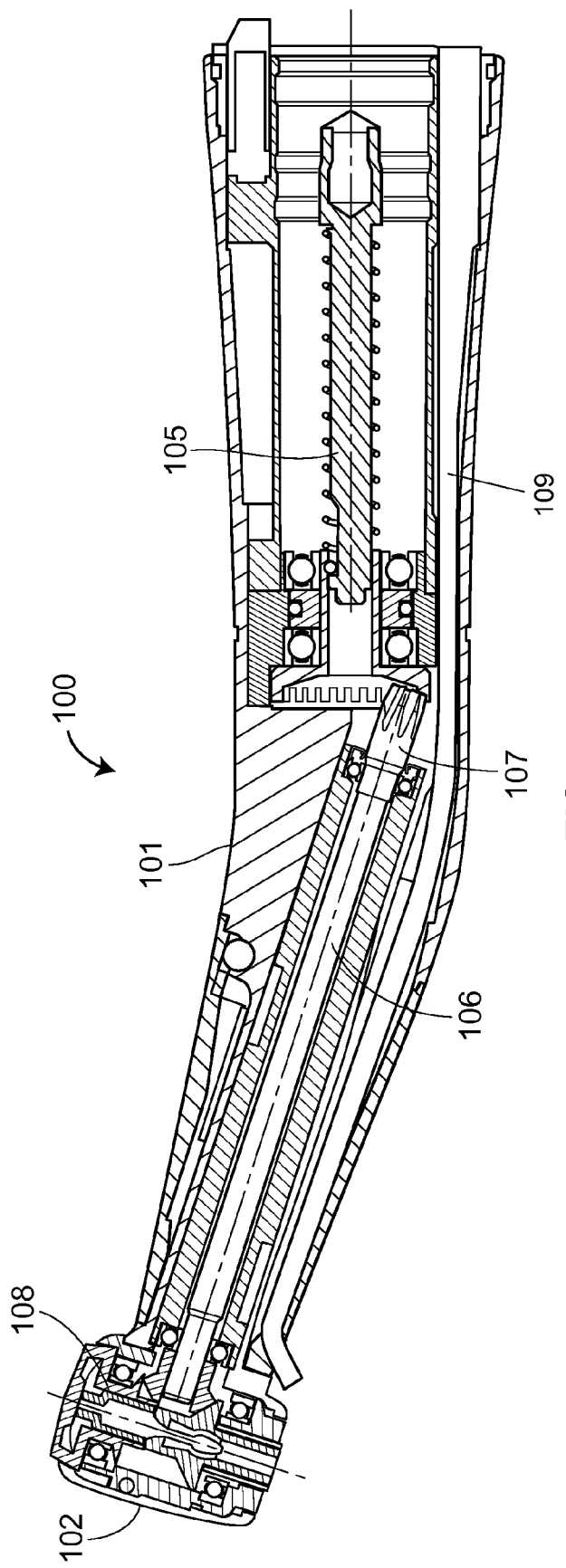
FIG. 7 shows a dental angled piece according to the prior art.

FIG. 1 shows a sectional representation of the knee region of a dental angled piece. This angled piece 1 corresponds substantially to the handpiece already known from the prior art as shown in FIG. 7. The angled piece 1 thus has an elongate handle sleeve 2 having a front head region 3, means for receiving a dental treatment tool, for example a drill, being provided inside the head region 3. The means for detachably mounting the drill are already known and, accordingly, are not explained in greater detail in the following.

A rotation of the drill is achieved by means of a drive train, which extends through the handle sleeve 2 and which, in particular, has two shafts 4 and 6, which are coupled to each other. The rear shaft 4 in this case is coupled to a drive mechanism, for example an electric motor, and the front shaft 6 transfers the rotation to the drill by means of a further transmission. By corresponding bearings, both shafts 4 and 6 are disposed so as to be rotatable inside the handle sleeve 2, the respective bearings 5 and 7 facing towards the coupling region being represented in FIG. 1.

Since an angled piece is represented in the present example, the two shafts 4 and 6 are not aligned parallel to each other, but are disposed at an angle. To ensure coupling of the rotary motion, a special transmission 8 is used, in which the first shaft 4 has an end-face gear wheel 9 having an internal toothing. This internal toothing 9 acts in combination with an end-face external toothing 10 on the front shaft 6. Thus far, the design of the drive train corresponds to that of the known handpiece according to FIG. 7.

A special feature of the handpiece 1 according to the invention resides in that a special sealing element 20 is used in the coupling region between the rear shaft 4 and the front shaft 6, the design of which sealing element can be seen, in particular, in FIGS. 2-5. This additional sealing element 20 is preferably composed of a slightly elastic material, is preferably realized as a single piece, and is inserted in a corresponding recess, or bore 11, of the handle sleeve 2. The sealing element 20 in this case has, firstly, a cylindrical lateral surface 21, which constitutes a first sealing surface and which is intended for bearing contact against the inner wall of the cylindrical bore 11. The seal in this case is improved in that the back end region of the lateral surface 21 is provided with a sealing bead 22.

Furthermore, the sealing element 20 has a first cylindrical extension 25, which likewise serves as a further sealing surface and extends from the lateral surface 21 in such a way that it is aligned substantially parallel to the rear shaft 4. This extension 25 is designed in such a way that it acts in combination with the front end region of an insert piece 12, which is pushed into the handle sleeve 2 from the back and which serves to stabilize the bearings 5 for the rear shaft 4 from the back and to fix the sealing element 20 in the bore 11. The combined action of the front end region of this insert piece 12 with the extension 25, which—according to the representation of FIG. 1—projects slightly into the end-face opening of the insert piece 12 and, preferably, is likewise provided with a sealing bead, constitutes a further sealing surface.

Finally, extending from the front side of the sealing element 20 there is also a second extension 26, via which a third seal is to be effected. This front extension 26 acts in combination with a receiving sleeve 13 for the front shaft 6 and is aligned at an offset, so that it runs parallel to the front shaft 6. The sleeve 13 for receiving the shaft 6 in this case is dimensioned in such a way that it extends into the inner region of this extension 26, as can be seen from FIG. 1.

The sealing element according to the invention thus preferably is formed of a single-piece sealing body, by which, ultimately, the three following sealing regions are achieved:

a first seal is effected by the bearing contact of the cylindrical lateral surface 21 on the inner surface of the bore 11;

a second seal is effected by the bearing contact of the rear cylindrical extension 25 on the inner surface of the axially adjoining insert part 12; and a third seal is effected by the bearing contact of the extension 26, aligned at a defined angle and having a preferably narrowing, step-like offset encircling in the manner of a ring, on the circumferential surface of the lateral surface of the sleeve 13 for mounting the shaft 6.

Figure 6:
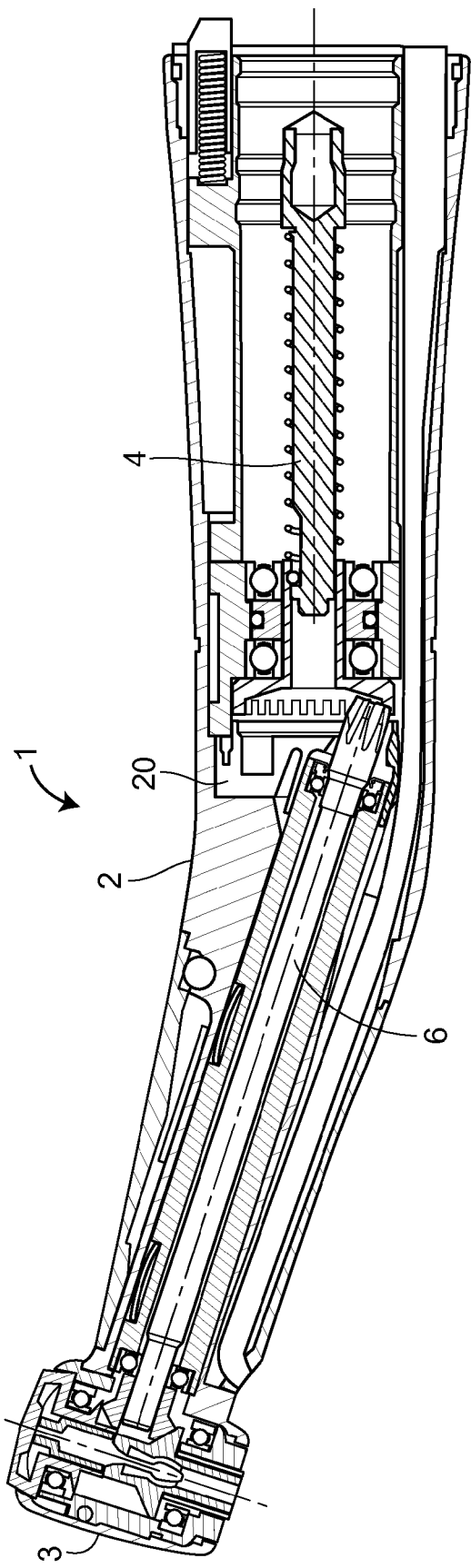
FIG. 6 shows a dental hand instrument having the sealing element according to the invention, in a lateral sectional representation.

Accordingly, the use of this single sealing element 20 enables an optimum seal to be achieved, in particular in the region of the coupling of the two shafts. As is further shown by a comparison of FIGS. 6 and 7, the use of this sealing element also results in a reduction of the size of the remaining cavity in the coupling region. This reduction in the volume of the functional space through which there is a flow results in a reduction in the need for re-oiling.

To ensure that the sealing element 20 is disposed in the correct position in the handle sleeve 2 of the handpiece 1, and thereby to ensure optimum sealing, it is possible to provide various measures by which a preferred disposition of the sealing element 20 is defined. In the present exemplary embodiment, two segment-type recesses 23 are provided in the lower region of the cylindrical lateral surface 21, which recesses act in combination with corresponding projections in the handle sleeve 2. In this way, it is ensured that the sealing element 20 is optimally disposed and oriented in the sleeve 2 and, accordingly, the sealing is effected in the desired manner. As an alternative to these recesses or depressions, it would also be possible to use elevations, bores, hollows, pins, balls or comparable measures.

Ultimately, the seal of the functional region in a handpiece is optimized considerably by the sealing element according to the invention. In this case, a particular advantage also consists in that the sealing element can easily be removed again and, accordingly, assembly or disassembly of the hand instrument is not impaired.

The invention claimed is:

1. Dental hand instrument having an elongate handle sleeve, at a front end of which there is disposed a tool holder for holding a treatment tool, there being disposed inside the elongate handle sleeve a driving mechanism for driving the treatment tool, the driving mechanism having two rotatably mounted shafts that are coupled to each other, and wherein a one-piece sealing element is disposed in a coupling region of the two rotatably mounted shafts inside the elongate handle sleeve, wherein the sealing element is enclosed within the elongate handle sleeve, the sealing element having a first cylindrical extension which is receivable in a cylindrical bore of the dental hand instrument, the first cylindrical extension having a first axis that is aligned with a first shaft of the two rotatably mounted shafts, the sealing element further having a second cylindrical extension configured to form a seal against a receiving sleeve for a second shaft, the second cylindrical extension having a second axis that is aligned with the second shaft of the two rotatably mounted shafts, and the first axis and second axis are oriented at a non-zero angle with respect to one another, the sealing element further having a cylindrical lateral surface spaced apart from the first cylindrical extension, and wherein the sealing element includes two segment-type recesses disposed in a lower region of the cylindrical lateral surface, the two segment-type recesses forming a cut-out portion of the cylindrical lateral surface proximate the second cylindrical extension.

2. Dental hand instrument according to claim 1, wherein the treatment tool is a dental drill.

3. Dental hand instrument according to claim 1, wherein the cylindrical lateral surface has a sealing bead extending from one end thereof.

4. Dental hand instrument according to claim 3, further comprising a receiving sleeve for one of the two rotatably mounted shafts, the receiving sleeve extending into an inner region of the second cylindrical extension.

5. Dental hand instrument according to claim 1, wherein the first cylindrical extension includes a sealing bead.

6. Dental instrument according to claim 1, wherein the sealing element is composed of a material that is sufficiently elastic to seal the cylindrical bore and a front sleeve portion.

7. Dental instrument according to claim 1, wherein the first and second axes intersect at a location that is outside of the sealing element.

8. Dental hand instrument having an elongate handle sleeve, at a front end of which there is disposed a tool holder for holding a treatment tool, there being disposed inside the elongate handle sleeve a driving mechanism for driving the treatment tool, the driving mechanism having two rotatably mounted shafts that are coupled to each other, and wherein a one-piece sealing element is disposed in a coupling region of the two rotatably mounted shafts inside the elongate handle sleeve, wherein the sealing element is enclosed within the elongate handle sleeve, the sealing element having a first cylindrical extension which is receivable in a cylindrical bore of the dental hand instrument, the first cylindrical extension having a first axis that is aligned with a first shaft of the two rotatably mounted shafts, the sealing element further having a cylindrical lateral surface spaced apart from the first cylindrical extension, the sealing element further having a second cylindrical extension forming a seal against a receiving sleeve for a second shaft, the receiving sleeve extending into an inner region of the second cylindrical extension, the second cylindrical extension having a second axis that is aligned with the second shaft of the two rotatably mounted shafts, and the first axis and second axis are oriented at a non-zero angle with respect to one another, wherein a first seal is effected by a bearing contact of the cylindrical lateral surface on an inner surface of the elongate handle sleeve, a second seal is effected by a bearing contact of the first cylindrical extension on an inner surface of an insert, and a third seal is effected by a bearing contact of the second cylindrical extension having a narrowing, step-like offset encircling in the manner of a ring, on a lateral surface of the receiving sleeve.

* * * * *